(12) United States Patent
Gallem et al.

(10) Patent No.: US 11,992,603 B2
(45) Date of Patent: May 28, 2024

(54) CONTROLLER FOR AN AEROSOL GENERATOR

(71) Applicant: PARI Pharma GmbH, Starnberg (DE)

(72) Inventors: Thomas Gallem, Munich (DE); Markus Reinhart, Utting (DE)

(73) Assignee: PARI Pharma GmbH, Starnberg (DE)

( * ) Notice: Subject to any disclaimer, the term of this patent is extended or adjusted under 35 U.S.C. 154(b) by 748 days.

(21) Appl. No.: 17/048,782

(22) PCT Filed: Apr. 18, 2019

(86) PCT No.: PCT/EP2019/060107
§ 371 (c)(1),
(2) Date: Oct. 19, 2020

(87) PCT Pub. No.: WO2019/202085
PCT Pub. Date: Oct. 24, 2019

(65) Prior Publication Data
US 2021/0113785 A1    Apr. 22, 2021

(30) Foreign Application Priority Data

Apr. 20, 2018  (EP) .................................... 18168479

(51) Int. Cl.
*A61M 11/00* (2006.01)
*B05B 12/00* (2018.01)
(Continued)

(52) U.S. Cl.
CPC .......... *A61M 11/005* (2013.01); *B05B 12/004* (2013.01); *B05B 12/08* (2013.01);
(Continued)

(58) Field of Classification Search
CPC ............ A61M 11/005; A61M 15/0085; A61M 2205/14; A61M 2205/3317;
(Continued)

(56) References Cited

U.S. PATENT DOCUMENTS 9,016,272 B2    4/2015  Gallem et al.
2012/0291777 A1*  11/2012  Gordon .................. B05B 15/14
324/649
(Continued)

FOREIGN PATENT DOCUMENTS

DE         19953317 C1      2/2001
DE    102005038619 A1       2/2007
(Continued)

OTHER PUBLICATIONS

International Preliminary Report on Patentability for International Application No. PCT/EP2019/060107 dated Oct. 29, 2020.
(Continued)

*Primary Examiner* — Michael J Brown
(74) *Attorney, Agent, or Firm* — Wolf, Greenfield & Sacks, P.C.

(57) ABSTRACT

The present invention relates to a controller for an aerosol generator having a vibration head for generating an aerosol, the controller comprising: a connection unit (110) for connecting an electric contacting element (300), the electric contacting element being connectable with the vibration head (210); a detection unit (120) for detecting an electric energy storage capacity parameter related to the connected electric contacting element (300); and a determination unit (130) for determining whether the vibration head (210) is connected with the electric contacting element (300) based on the determined electric energy storage capacity parameter.

14 Claims, 10 Drawing Sheets

(51) Int. Cl.
*B05B 12/08* (2006.01)
*B05B 17/00* (2006.01)
*B05B 17/06* (2006.01)
*G05B 19/042* (2006.01)
*A61M 15/00* (2006.01)

(52) U.S. Cl.
CPC ...... *B05B 17/0646* (2013.01); *B05B 17/0653* (2013.01); *G05B 19/042* (2013.01); *A61M 15/0085* (2013.01); *A61M 2205/14* (2013.01); *A61M 2205/3317* (2013.01); *A61M 2205/3368* (2013.01); *A61M 2205/581* (2013.01); *A61M 2205/582* (2013.01); *A61M 2205/583* (2013.01); *A61M 2205/6018* (2013.01); *A61M 2205/6027* (2013.01); *A61M 2205/70* (2013.01); *A61M 2205/8262* (2013.01); *G05B 2219/25257* (2013.01)

(58) Field of Classification Search
CPC ...... A61M 2205/581; A61M 2205/582; A61M 2205/583; A61M 2205/6018; A61M 2205/6027; A61M 2205/70; A61M 2205/8262; B05B 12/004; B05B 12/08; B05B 17/0646; B05B 17/0653; G05B 19/042; G05B 2219/25257
USPC ......................................................... 700/280
See application file for complete search history.

(56) References Cited

U.S. PATENT DOCUMENTS

| | | |
|---|---|---|
| 2013/0291859 A1 | 11/2013 | Casey et al. |
| 2018/0070641 A1* | 3/2018 | Batista ................. A61M 11/042 |
| 2019/0045844 A1* | 2/2019 | Reevell ................. A61M 15/06 |
| 2020/0316325 A1* | 10/2020 | Reevell ................. A24F 40/53 |

FOREIGN PATENT DOCUMENTS

| | | |
|---|---|---|
| DE | 102006006183 A1 | 8/2007 |
| DE | 102007056462 A1 | 5/2009 |
| DE | 102008022987 A1 | 11/2009 |
| DE | 102008054431 B3 | 6/2010 |
| EP | 0615470 A1 | 9/1994 |
| EP | 1295647 A1 | 3/2003 |
| EP | 1386672 A1 | 2/2004 |
| EP | 2910268 A1 | 8/2015 |
| EP | 2957349 A1 | 12/2015 |
| EP | 2987520 A1 | 2/2016 |
| WO | WO 93/10910 A1 | 6/1993 |
| WO | WO 2012/026963 A2 | 3/2012 |

OTHER PUBLICATIONS

International Search Report and Written Opinion for International Application No. PCT/EP2019/060107 dated Jul. 19, 2019.

* cited by examiner

MEASUREMENT WITH VIBRATION HEAD

MEASUREMENT WITHOUT VIBRATION HEAD

CONTROLLER FOR AN AEROSOL GENERATOR

RELATED APPLICATIONS

This Application is a national stage filing under 35 U.S.C. 371 of International Patent Application Serial No. PCT/EP2019/060107, filed Apr. 18, 2019, entitled "CONTROLLER FOR AN AEROSOL GENERATOR". Foreign priority benefits are claimed under 35 U.S.C. § 119(a)-(d) or 35 U.S.C. § 365(b) of European application number 18168479.6, filed Apr. 20, 2018. The entire contents of these applications are incorporated herein by reference in their entirety.

TECHNICAL FIELD

The present invention relates to a controller for an aerosol generator, and in particular to a controller for an aerosol generator for detecting a connection of a vibration head of the aerosol generator and/or for identifying a vibration head type being connected with the controller.

BACKGROUND

Aerosols for therapeutic purposes are generated and delivered to a desired location within a user's or patient's body with an aerosol delivery device. A fluid or liquid (including a medicament or drug) to be aerosolized or nebulized is supplied to an aerosol generator, the fluid or liquid is aerosolized or nebulized by the aerosol generator and the resultant aerosol is delivered to the user or patient.

The fluid or liquid may be aerosolized or nebulized in the aerosol generator by a vibratable element which is referred to as a vibratable head or vibration head in the following. Such a vibration head is provided at least with a membrane and an oscillation generator or vibration generating element, such as a piezoelectric element. The characteristics (mechanical and/or electrical) of the vibration head of the aerosol generator are decisive for the quality of the generated aerosol. At the same time, the vibration head is also generally very sensitive. For example, a misalignment of the vibration head may negatively affect the oscillatory or vibration motion of the vibration head during aerosol generation and therefore compromise the quality of the generated aerosol and the dosage accuracy.

Figure 1A:
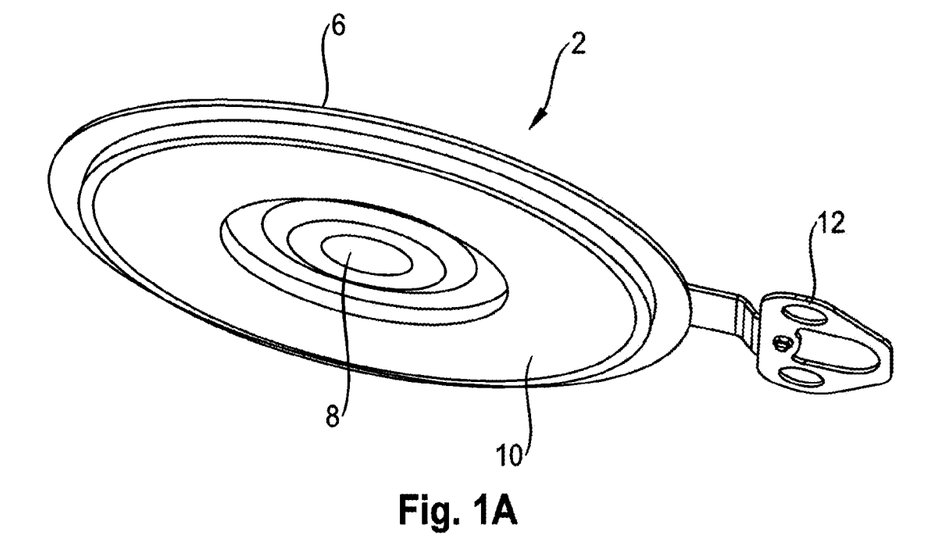
FIGS. 1A and 1B show a schematic perspective bottom view and top view of a vibration head of an aerosol generator, respectively.
Figure 1B:
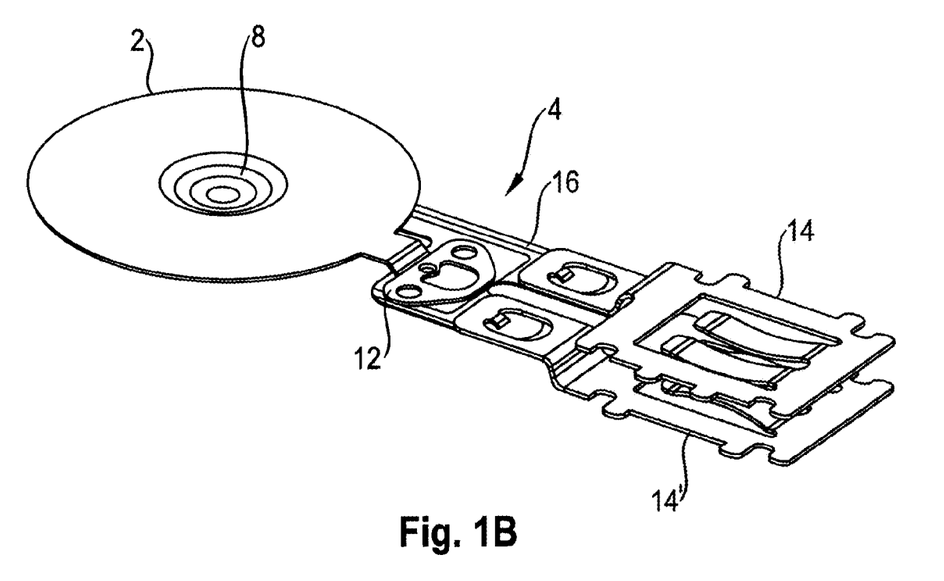

FIGS. 1A and 1B show a schematic perspective bottom view and top view of an example of a vibration head of an aerosol generator as disclosed in EP 2 957 349 A1. Here, the front portion 2 of a vibratable element 4 has a support member 6, a vibratable membrane 8 with a plurality of holes (not shown), an annular vibration generating element 10, e.g. a piezoelectric element, and a connection portion 12. The piezoelectric element 10 serves as a vibrator for vibrating the vibratable membrane 8. In operation, an aerosol (i.e. liquid droplets) are generated on one side of the vibratable membrane 8 from a liquid or fluid that is provided on the other side of the vibratable membrane. Further, the vibration head may comprise a pair of electric contacts 14, 14', e.g., plugs for connecting to a controller (not shown). As shown here, the electrical contacts 14, 14' are punched out from a stainless steel sheet and are subsequently bent, i.e. bent into the shape as shown in FIG. 1B. The electrical contacts may be connected to the connection member 12 and the piezoelement 10 through a flexible strip conductor 16, such as a printed board track or a strip line. While FIG. 1A illustrates a case in which the support member 6 and the vibratable membrane are provided as an integrated element, this is not a limiting configuration, and a vibration head may also be provided without such a support member.

Figure 2A:
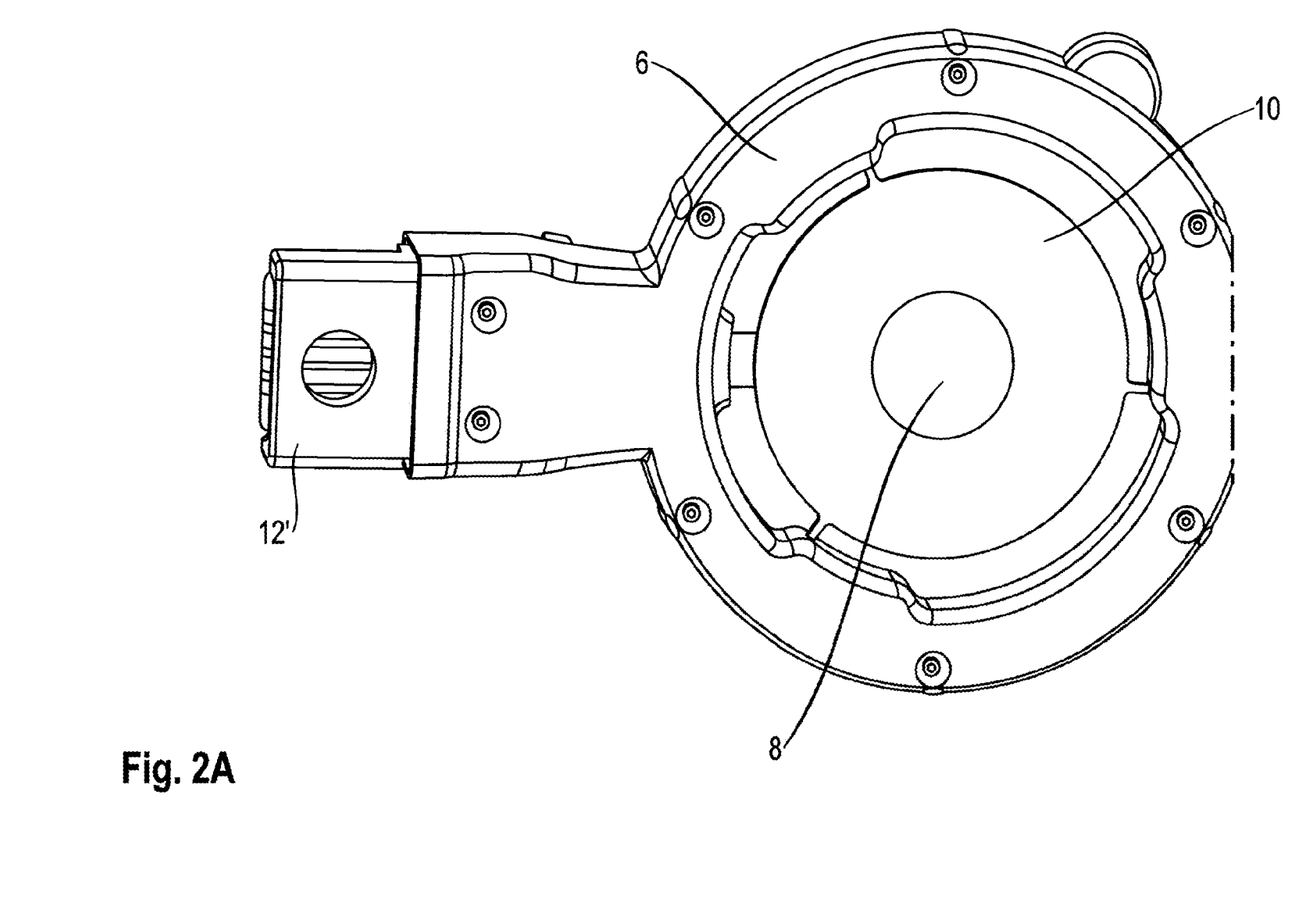
FIGS. 2A and 2B show a schematic perspective top view and side view of another vibration head of an aerosol generator respectively.
Figure 2B:
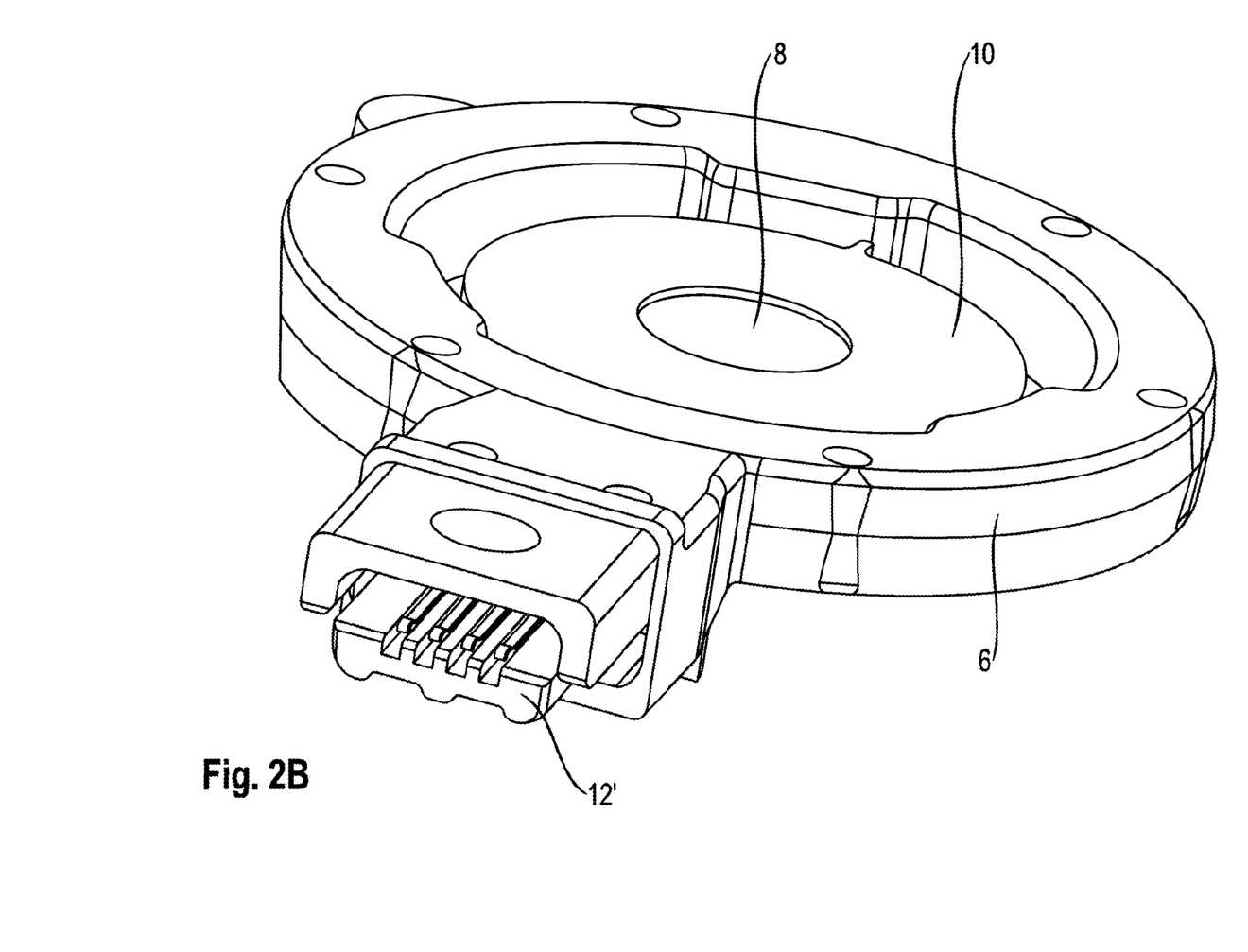

Here, the electrical contacts 14, 14' for the vibration head are not restricted to the example shown in FIG. 1B and may, for example, be constructed in a way such that a multiple-pin connection cord for an electric connection with the controller may be connected. FIGS. 2A and 2B show a schematic perspective top view and side view of a vibration head of an aerosol generator including a support member 6, a vibratable membrane 8, and an annular piezoelement 10, and a connecting unit 12' for connecting a 4-pin connection cord with the controller. An appropriate placement and electrical connection of the vibration head in the aerosol generator is decisive for securing a sufficiently high quality of the generated aerosol.

Problems with Existing Solutions

There are situations in which it is useful to provide a feedback as to a proper electrical connection of a vibration head with the controller. For example, this is helpful for patients in a hospital or emergency room environment which themselves are not capable of verifying the aerosolization, for example, when a medication or drug is delivered via a respiratory device. In order to reduce errors, it would therefore be desirable to provide a feedback as to a proper electrical connection of a vibration head with the controller.

SUMMARY

Therefore a need exists in the art for the controller to determine a proper connection of a vibration head of the aerosol generator.

Further, a variety of different vibration head types may be provided. Such vibration head types may be specifically designed for different medical applications, may have different electrical properties, and may therefore require different electrical drive parameters (such as voltage, current, frequency, and the like). Therefore, another need exists in the art for the controller to determine the type of vibration head that is provided in the aerosol generator and is electrically connected with the controller.

The features of a controller for an aerosol generator having a vibration head for generating an aerosol according to the present invention are defined in claim 1. Advantageous embodiments are described in the dependent claims.

DESCRIPTION OF THE EMBODIMENTS

Embodiments of the present invention are described with reference to the Figures. It is noted that the following description should not be construed as limiting the invention. In the following and the above, similar or same reference signs indicate similar or same elements or operations.

Figure 3:
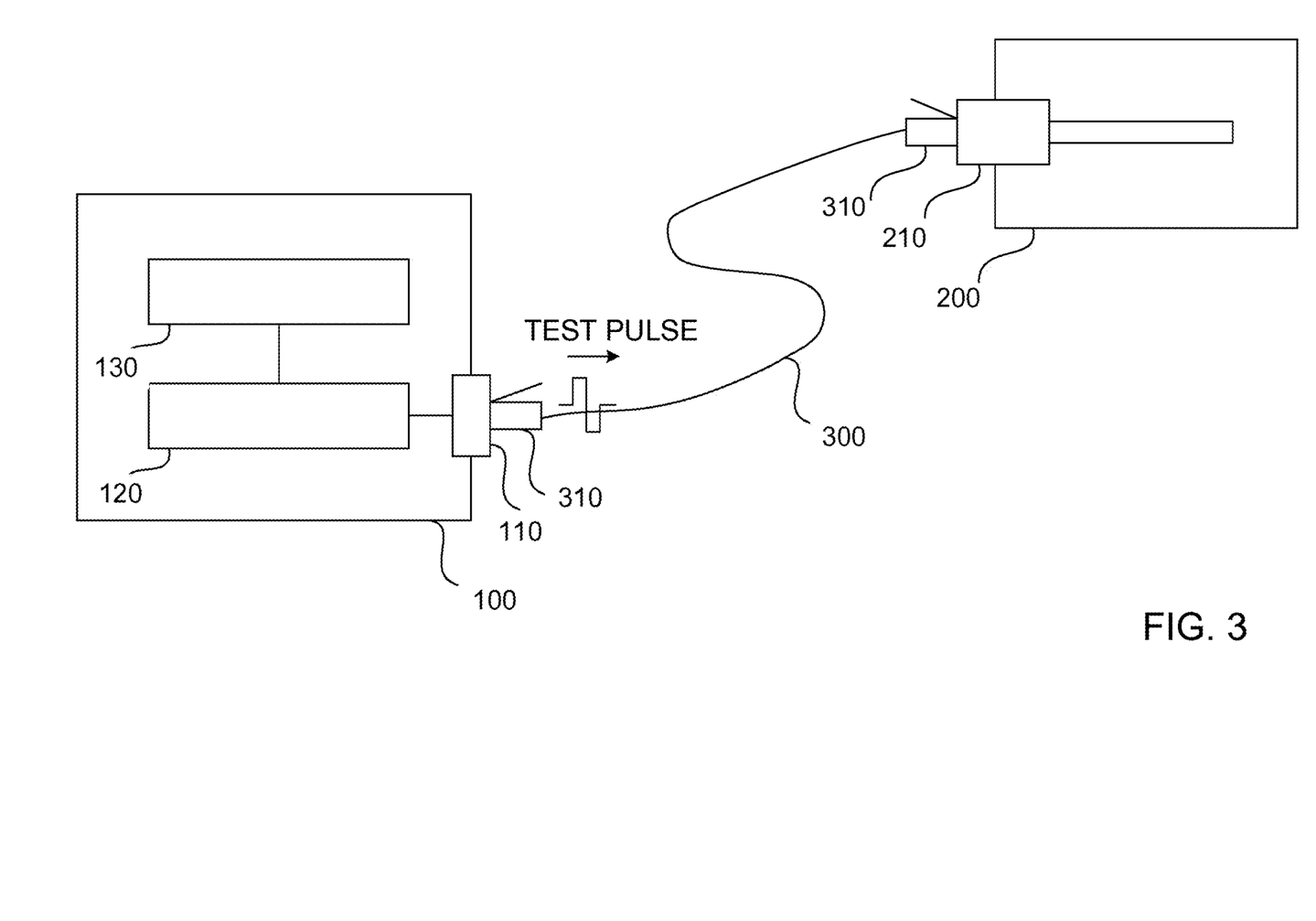
FIG. 3 shows a controller for an aerosol generator according to an embodiment of the present invention.

FIG. 3 shows a controller 100 according to an embodiment of the present invention, the controller being configured to determine whether a vibration head 210 of an aerosol generator 200 has been properly connected. In other words, the controller 100 is configured to detect whether a vibration head 210 is electrically connected and an aerosol generation is thus possible. Here, the vibration head 210 is provided within the aerosol generator 200. For generating aerosol, the vibration head 210 may comprise at least a membrane and a vibration generating element, such as a piezoelectric element, as detailed above. Further, it is noted that the vibration head 210 is insertable into the aerosol generator 200, and may thus be replaced with another vibration head of the same or a different type. The mechanical placement, appropriate orientation, and the like of the vibration head 210 within the aerosol generator, for example with regard to a liquid reservoir is known to the skilled person, see, for example, EP 2 957 349 A1.

As further shown in FIG. 3, the controller 100 is provided with a connection unit 110, a detection unit 120, and determination unit 130.

The connection unit 110 of FIG. 3 is configured to connect an electric contacting element 300. The electric contacting element 300 may be at least one of an electronic cable, a connector, a connection cord, a print circuit, a circuit path, a conductive polymer, an electric wire, a pin, and a plug. For simplifying the understanding, FIG. 3 schematically illustrates a connection cord as the electric contacting element 300. As further schematically illustrated in FIG. 3, the electric contacting element 300 may be provided with a multiple-pin plug 310 or the like in order to provide an electrical connection with the connection unit 110. As shown, the electric contacting element 300 may also be electrically connected with the vibration head 210, e.g. via a multiple-pin plug 310 or the like, in order to provide a secure electric connection between the controller 100 and the vibration head 210, for example for the purpose of electrically driving the vibration head 210 in accordance with specific electric parameters for generating an aerosol. The electric contacting element 300 may therefore be connectable with both the controller 100 and the vibration head 210, or may have a fixed connection with the controller and is only connectable with the vibration head 210.

The detection unit 120 of FIG. 3 is configured to detect an electric energy storage capacity parameter related to the connected electric contacting element 300. Further, the determination unit 130 of FIG. 3 is configured to determine whether the vibration head 210 is connected with the electric contacting element 300 based on the determined electric energy storage capacity parameter.

Such a detection and determination mechanism may be of interest for patients in intensive medical care, for which a medication or drug administration is provided via a respiratory device, and which themselves are not capable of verifying the proper/correct aerosolization of the medication or drug. Therefor such a detection and determination mechanism may be of particular interest for health care providers (HCP), physicians, nurses, study nurses, which work in the field of hospitals or especially an intensive medical care units and therewith connected data banks and cloud systems. In addition, such an intensive medical care setup may require the presence of rather long electrical cables that connect the controller 100 with the aerosol generator 200 (being provided with an inserted vibration head 210) and which are thus prone to disconnection errors.

Therefore, a determination as to a correct connection of the vibration head 210 minimizes errors in medical treatments. Such a detection and determination mechanism may also be of particular interest in situations in which the controller is in a remote position from the aerosol generator (being provided with an inserted vibration head 210). In such a situation, the proper connection may, for example, not be visually checked.

In the following, two cases are distinguished. In a first case, the electric contacting element 300 is connected only with the connection unit 110 of the controller 100, while in a second case the electric contacting element 300 is connected with both the connection unit 110 of the controller 100 and the vibration head 210. Only in the second case, the vibration head 210 has an electric connection with the controller 100 and a proper aerosol generation can be ensured.

The present inventors have realized that the controller 100 itself is able to distinguish between these two cases on the basis of an electric energy storage capacity parameter. Here, the electric energy storage capacity parameter is associated or related to the connected electric contacting element 300 in the above first case, and is associated or related to the connected electric contacting element 300 and the connected vibration head 210 in the above second case. The electric energy storage capacity refers to at least one of an electric capacity (electric charge) and inductance (magnetic field energy) that may be stored in the vibration head 210 and the electric contacting element 300, respectively.

Figure 4A:
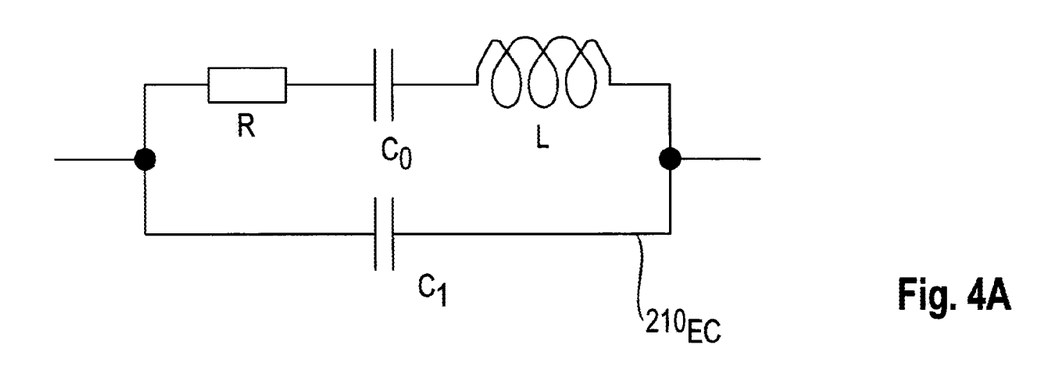
FIGS. 4A and 4B show equivalent electric circuit diagrams for a piezoelectric element and an electric cable, respectively.
Figure 4B:
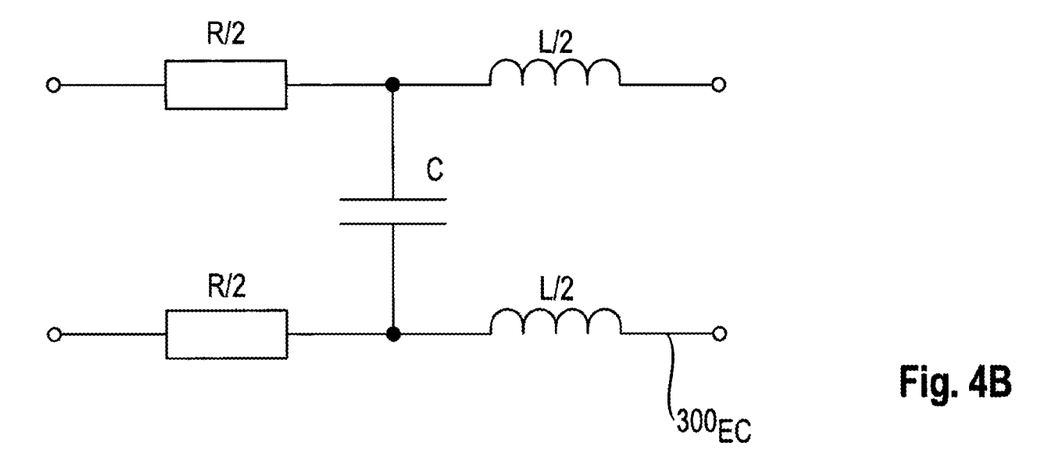

FIGS. 4A and 4B show equivalent electric circuit diagrams of the piezoelectric element of the vibration head 210 (FIG. 4A) and an electric cable as an example of the electric contacting element 300 (FIG. 4B). Here, according to the equivalent circuit $210_{EC}$ in FIG. 4A, the piezoelectric element of the vibration head 210 may be considered as having an electric energy storage capability due to capacitive ($C_0$, $C_1$) and inductive (L) circuit elements in FIG. 4A. Also, according to the equivalent circuit $300_{EC}$ in FIG. 4B, the electric cable (electric contacting element) may be considered as having an electric energy storage capability due to the capacitive (C) and inductive (L/2, L/2) circuit elements in FIG. 4B. The storage type of a piezoelectric element in a vibration head 210 may be primarily of capacitive nature with values of 4-7 nF. The storage type of an electric cable (electric contacting element) may be primarily of capacitive nature with values of 0.05-0.25 nF. In other words, both the vibration head 210 and the electric contacting element 300 have distinguishable electric energy storage capacities and thus define distinguishable parameters.

Based on the above, in the above first case, the electric energy storage capacity related to the connected electric contacting element 300 is thus the electric energy storage capacity of the electric contacting element 300. In the above second case, i.e. when also the vibration head 210 is connected, then the electric energy storage capacity related to the connected electric contacting element 300 is the electric energy storage capacity of both the electric contacting element 300 and the vibration head 210, i.e. the amount of electric energy that may be stored in both the electric contacting element 300 and the vibration head 210.

As will be further detailed below, the detection of a parameter related to the electric energy storage capacity may be performed by a pulsed measurement, for example by a mono-polar or bi-polar electric pulse measurement. This may be considered as a test pulse measurement. The mono-polar test pulse may be provided by a simple pulse generating set up, while a bi-polar test pulse is advantageous in order to electrically discharge the piezoelectric element of the vibration head 210 completely. Here, responsive to applying an electrical test pulse to the connected electric contacting element 300, an electric discharge profile, i.e. an electric discharge curve over a defined electric load in the first case (only electric contacting element connected) or second case (electric contacting element and vibration head connected), may be detected by the detection unit 120. Such electric discharge curves may be a voltage discharge profile typically having an exponential temporal decay $U_m(t)=U0\times \exp(-t/\tau)$ in which U is a measured voltage, t is time, and $\tau$ is an example of an electric energy storage capacity parameter that indicates a relevant capacitance and/or inductance value of the connected load. In the above first case in which only the electric contacting element 300 is connected, the electric energy storage capacity parameter $\tau 1$ is thus a value that is typically much smaller than in the above second case in which also the vibration head 210 is connected and the electric energy storage capacity parameter is $\tau 2$, i.e. $\tau 1 < \tau 2$.

Figure 5:
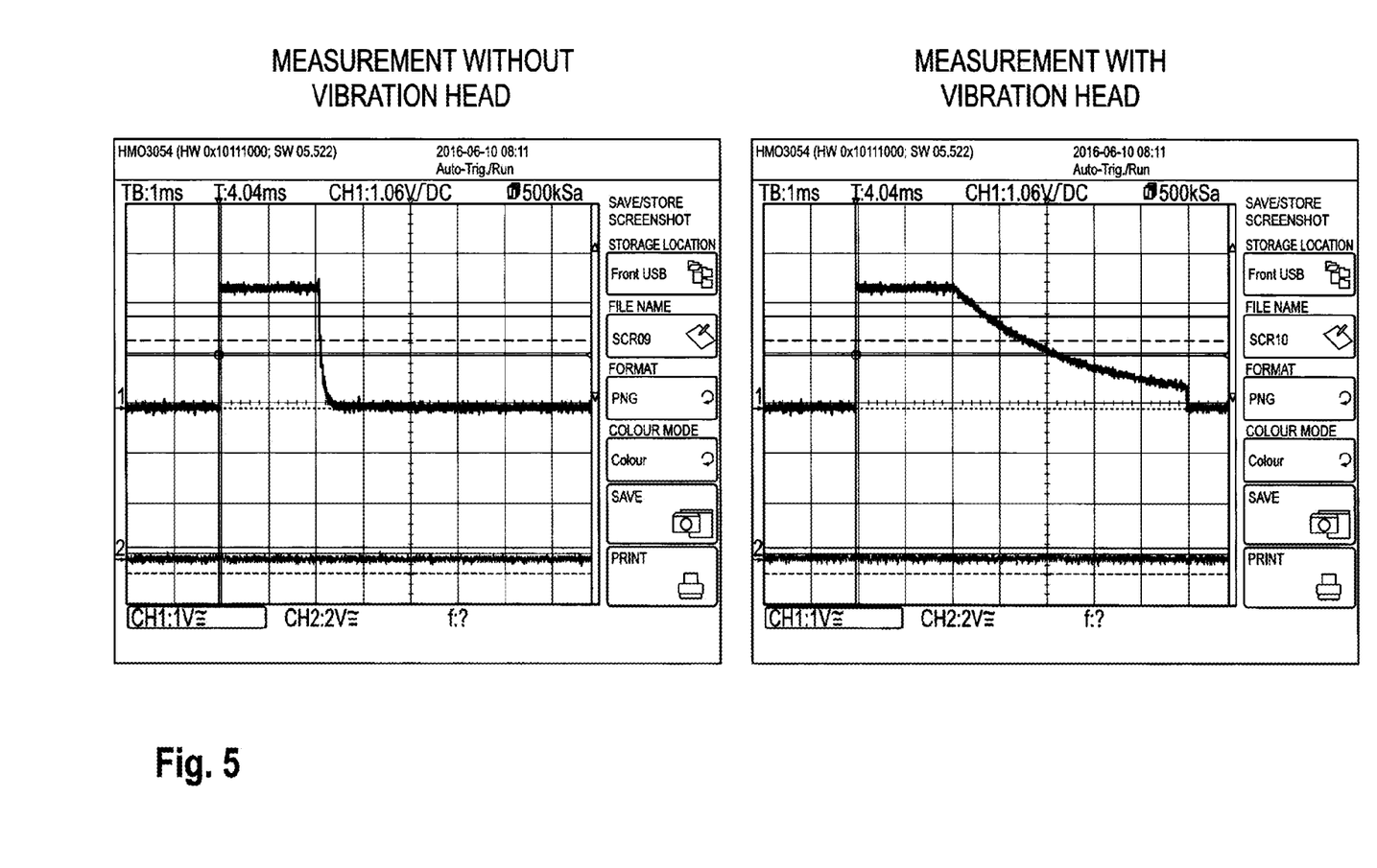
FIG. 5 shows a comparison of experimentally obtained electric discharge curves for a measurement with and without a vibration head.

FIG. 5 shows a comparison of experimentally obtained electric discharge curves for the first and second case. For the first case (left image), the measurement is performed without a connected vibration head. For the second case (right image), the measurement is performed with a connected vibration head. Discharge time constants $\tau 1$ without vibration head are typically about 0.2 ms, while discharge time constants $\tau 2$ with a connected vibration head are typically larger than 2 ms. The comparison in FIG. 5 conclusively shows that the electric discharge curve is distinguishably slower for the second case (i.e. $\tau 1 < \tau 2$) which confirms that the detection of a connected vibration head may be reliably performed by determining an electric energy storage capacity parameter.

More specifically, the determination unit 130 may thus be configured to analyze the measured discharge curve and determine an electric energy storage capacity parameter therefrom. Here, the analysis of the measured discharge curve may be performed by the determination unit 130 by applying one or more fitting parameters to the measured discharge curve. Based on the determined electric energy storage capacity parameter ($\tau 1$, $\tau 2$), the determination unit 130 thus determines whether the vibration head 210 is connected ($\tau \approx \tau 2$) or whether the vibration head 210 is not connected ($\tau \approx \tau 1$). Thus, determination may be performed by comparing the detected electric energy storage capacity parameter with a predetermined threshold. Such a predetermined threshold may be set on the basis of typical values $\tau 1$ for the electrical contacting element. It is noted that different electrical contacting elements (electronic cable, a connector, a print circuit, a circuit path, a conductive polymer, an electric wire, a pin, a plug, or a combination thereof) may be used in practical applications, but that the electric energy storage capacity parameter of a vibration head is always significantly larger, as explained above.

The above measurement may be performed during the regular activation of the vibration head, i.e. an electric activation of the vibration head when an aerosol is generated (online operation), and may also be performed in a pre-phase (i.e. a starting phase) of the aerosol generation activation, or during a stand-by mode in which no aerosol is generated. During the stand-by operation, for example, a pulsed electric excitation of the vibration head (via the electric contacting element 300) uses electric parameters (voltage, current) which are not sufficient to vibrate the vibration head 210 in a way to generate aerosol. Such a stand-by measurement avoids, for example, an actual aerosol generation and associated drug loss that results from an operation of the aerosol generator during an on-line operation in which the vibration head is supplied with alternating current. In this way, no liquid medication is wasted when it is determined (only) that a proper electric connection of the vibration head 210 is achieved.

In another embodiment, the determination unit 130 may be further configured to determine a vibration head type. As discussed above, different vibration head types may be provided for the aerosol generator 200. In particular, different electrical parameters may be required for the different vibration head types so that the determination of the connected vibration head type enables the controller 100 to select and apply corresponding control and/or drive parameters (voltage, current, and/or frequency).

Figure 6:
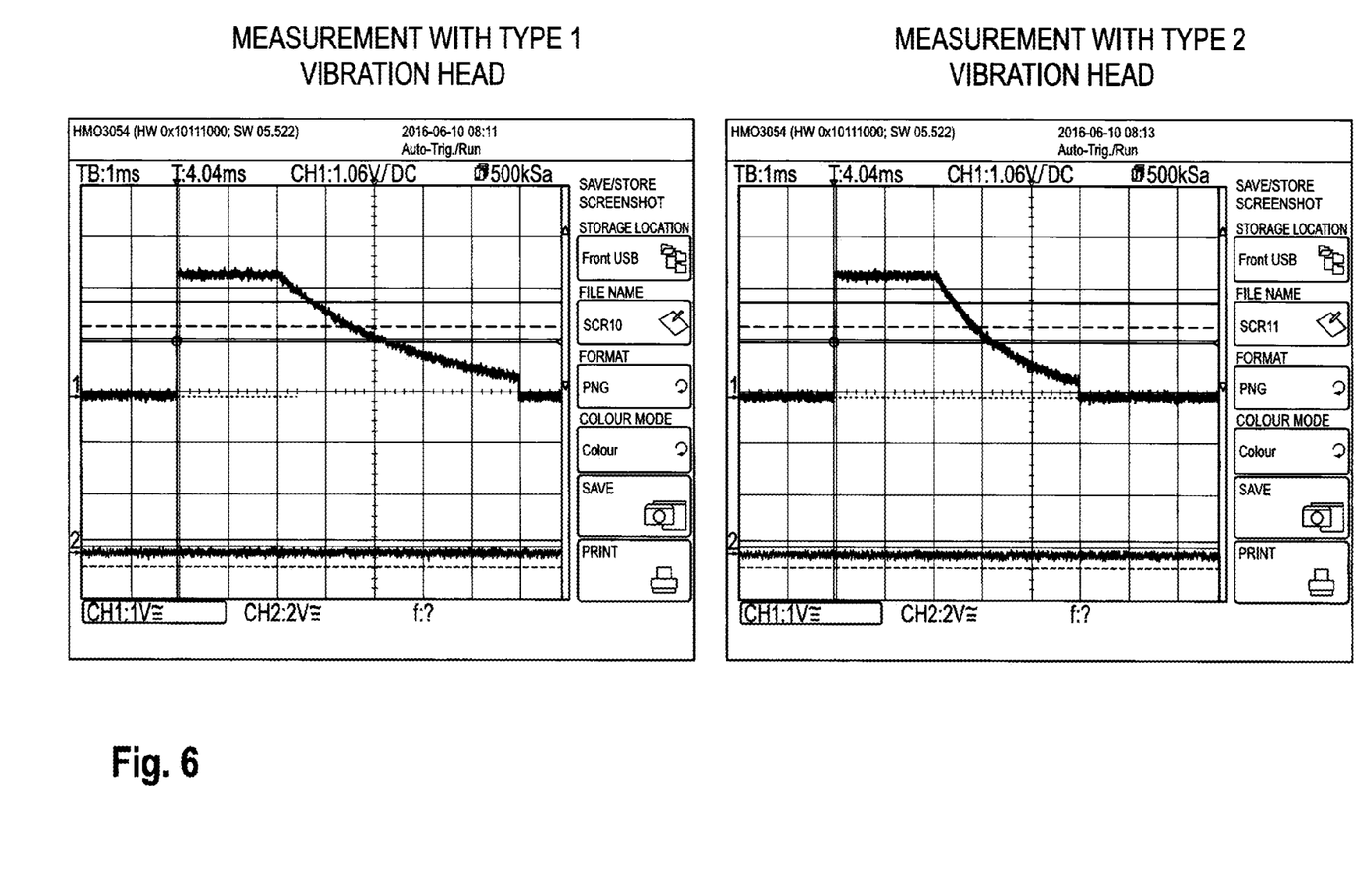
FIG. 6 shows a comparison of experimentally obtained electric discharge curves for a measurement with different vibration head types.
Figure 9:
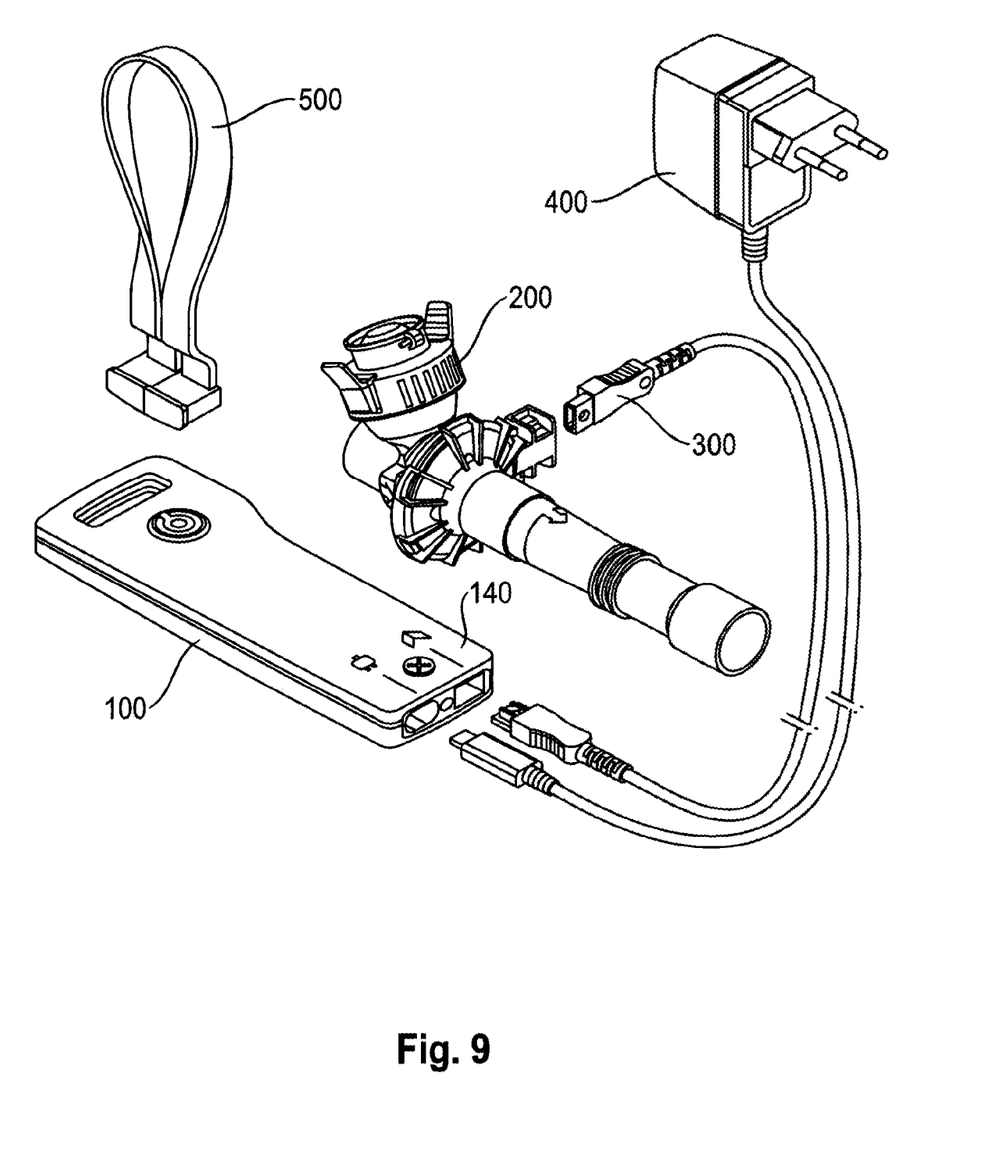
FIG. 9 shows a controller for an aerosol generator according to another embodiment of the present invention.

The determination unit 130 may distinguish between a plurality of different vibration head types on the basis of the detected electric energy storage capacity parameter. FIG. 6 shows a comparison of experimentally obtained electric discharge curves when 2 different vibration head types, here Type 1 vibration head and Type 2 vibration head, are connected. Here, a Type 1 vibration head may be related to a vibration head as illustrated in FIGS. 2A, 2B, and 9. Such a Type 1 vibration head may be used in "closed" or "inline" systems (see below), and may be provided with spring spokes for centrally holding the membrane in a vibration-optimized manner and may be casted in a soft plastic (see FIGS. 2A, 2B) to seal the housing, see, for example, DE 10 2005 038619, DE 10 2007 056462, DE 10 2008 054431, DE 10 2006 006183, DE 10 2008 022987. Further, such a Type 2 vibration head may be related to a vibration head as illustrated in FIGS. 1A, 1B, and may be mechanically integrated into a hard plastic assembly forming a single entity with the liquid/fluid reservoir, see, for example, EP 2 910 268, EP 2 957 349, EP 2 987 520, U.S. Pat. No. 9,016,272. Another types of vibration heads, for example as illustrated in EP 0 615 470, EP 1 295 647, DE 1 995 3317, and EP 1 386 672, may also be distinguished accordingly.

Here, the comparison indicates that the discharge time constants for the Type 1 vibration head and Type 2 vibration head may be distinguished. In particular, the Type 1 vibration head has a larger discharge time constant. For each connected vibration head type a distinguishable electric discharge curve can thus be obtained. Based on this experimental insight, the determination unit 130 may be provided with respective ranges for the electric energy storage capacity parameter that are vibration head specific. In other words, these ranges may be specific for different vibration heads to uniquely identify the respective vibration head type. For example, for the above Type 1 vibration head, a specific parameter range between a minimal (min) and maximum (max) value may be provided, i.e. $\tau 2$ (Type 1, min) $\tau 2 \leq \tau 2$ (Type 1, max), and a specific parameter range may also be provided for the above Type 2 vibration head, i.e. τ2 (Type 2, min) τ2≤τ2 (Type 2, max). The determination unit 130 may then determine the connected vibration head 210 by comparing the detected electric energy storage capacity parameter τ2 with these ranges.

Figure 7:
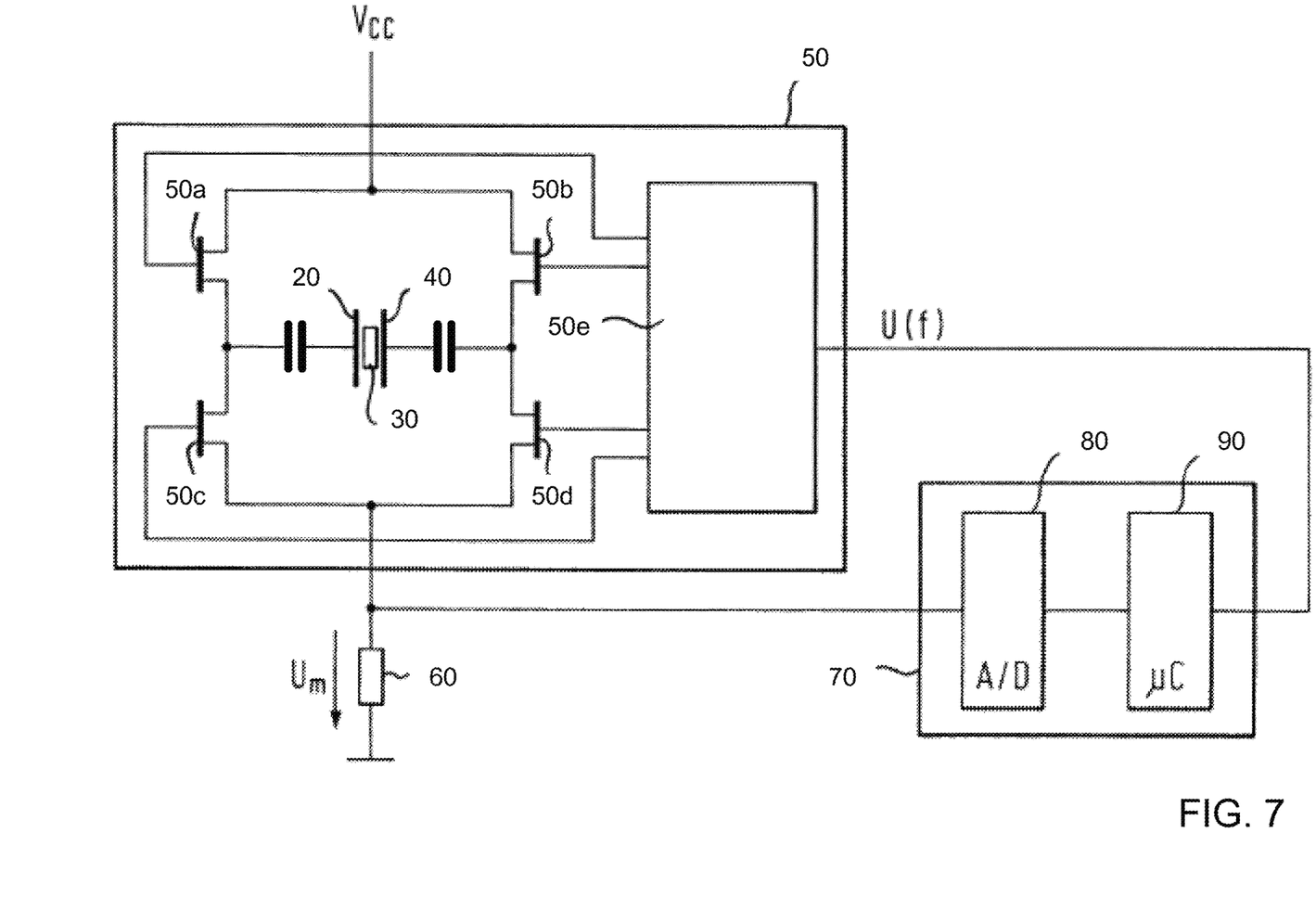
FIG. 7 shows an example of an electric circuit diagram usable for implementing an embodiment of the present invention.

FIG. 7 shows an example of an electric circuit diagram usable for implementing an embodiment of the present invention. In particular, when it is determined by the controller that the vibration head is electrically connected, then the controller operates to drive the vibration head and to vibrate the vibration head at a predetermined frequency f. It is noted that different vibration head types may operate with different predetermined frequencies f, and that the above identification of the connected vibration head type enables the controller to select and use the appropriate drive parameters (which will be further discussed below). FIG. 7 schematically illustrates the piezoelectric element 30 as well as electrodes 20 and 40 of the oscillation generator (vibration generating element) of the vibration head. The control unit (further described below) of the controller may include a drive element 50 supplying AC voltage to the electrodes 20 and 40 for the piezoelectric element 30. Here, the drive element 50 may include an FET-bridge 50a, 50b, 50c, and 50d and a voltage-controlled oscillator (VCO) or controller element 50e for driving the FET-bridge. The vibration frequency f of the piezoelectric element 30 is determined by an input voltage U(f) into the VCO or a frequency-dependent control signal into the controller element 50e.

FIG. 7 further shows a sensor element 60 (detection unit), e.g. a resistor, for measuring the above described voltage discharge, e.g. $U_m(t)=U0\times\exp(-t/\tau)$. This sensor signal is supplied to the control element 70 (determination unit) comprising, e.g., an A/D converter 80 for converting the sensor signal into digital values and providing these to a microcontroller 90. The microcontroller 90 evaluates the digital values, determines an electric energy storage capacity parameter, as explained above, therefrom, and thus determines whether the vibration head is connected with the electric contacting element and/or the vibration head type.

The microcontroller 90 may be a programmable module which can be used in the implementation of control and regulation tasks. The microcontroller 90 provides the computing power and the programmability required for analyzing the discharge profile $U_m(t)$ and thus determining electric energy storage capacity parameters. In addition, the microcontroller 90 may be programmed to generate a control signal U(t) that leads to a mono-polar or bi-polar electric test pulse. In the microcontroller 90, in addition to a computing unit and/or a logic unit, one or more storage units may be provided for the volatile and non-volatile storage of data. Instead of a microcontroller, a microprocessor with corresponding peripheral circuits or other programmable devices can also be used.

Figure 8:
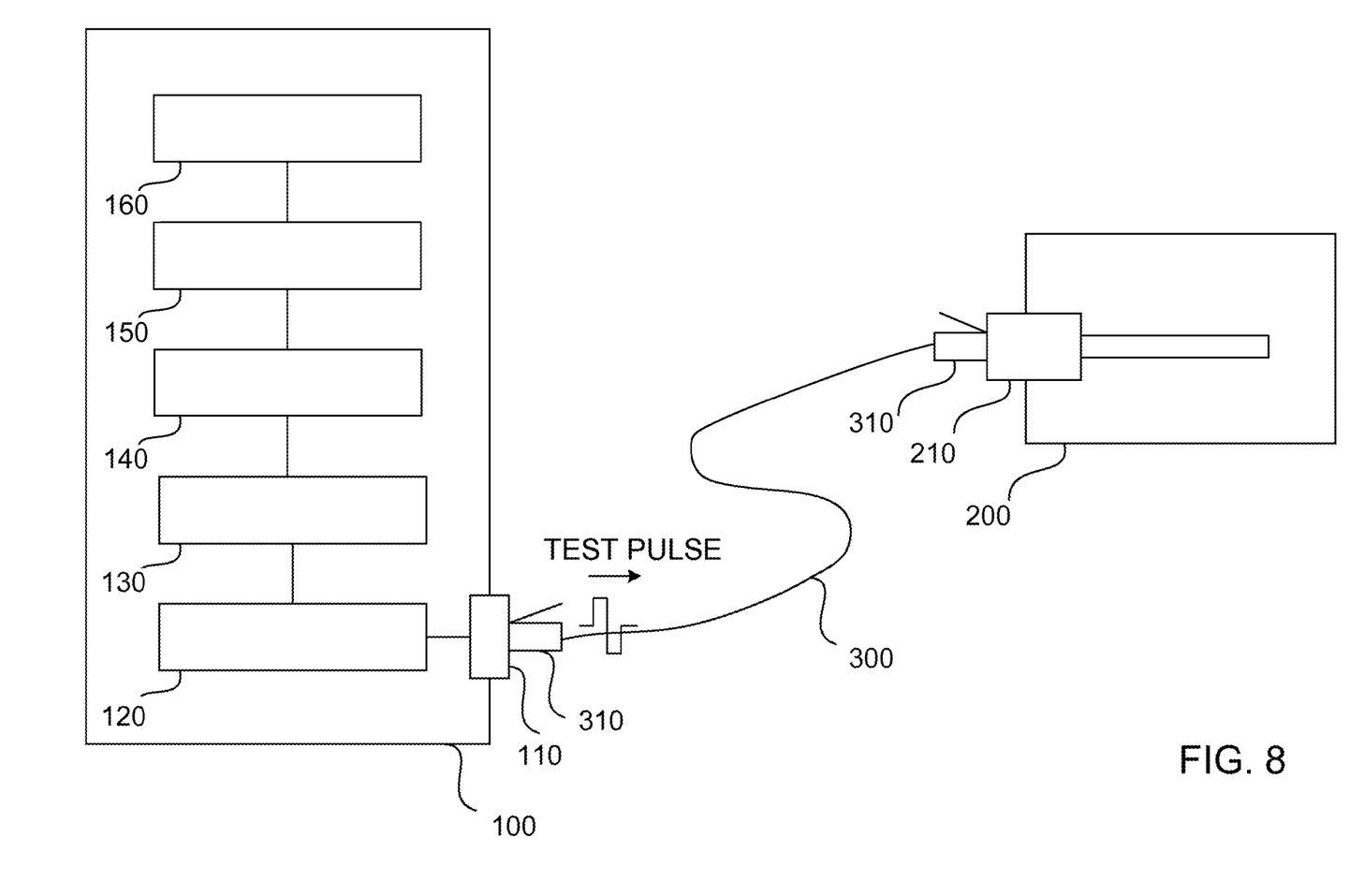
FIG. 8 shows a controller for an aerosol generator according to another embodiment of the present invention.

FIG. 8 shows another embodiment of the controller 100. In addition to the embodiment illustrated in FIG. 3, the controller 100 may further be provided with a notification unit 140, a storage unit 150, and a controlling unit 160.

The notification unit 140 is configured to notify a user, via at least one of a visual, audio, or a haptic feedback, of a determination result of the determination unit 130. For example, if a vibration head 210 is connected a green light may be shown to the user, while a red (e.g., blinking) light is shown to the user if the determination result indicates that a vibration head 210 is not connected. In particular, the notification may provide a warning that a vibration head is not connected with the controller and therefore the aerosol generation cannot be accomplished. This is, for example, helpful in hospital environments in which rather long electric cables are used and the proper electric connection between the controller and the vibration head is lost due to obstacles or the like. Alternatively, or in addition, notification unit 140 may send a communication message, e.g. an e-mail, SMS, warning signal, or the like, to a third party (e.g. a central hospital monitoring system or the like).

According to a further embodiment the determination unit 130 may be further configured to determine water ingress into the vibration head 210. Water ingress into the vibration head 210, for example into a contact region with the electric contacting element 300 and/or into a region of the piezoelectric element of the vibration head 210, may result in a short circuit pre-stage in which the proper electric operation of the vibration head is at least impaired. In such a situation, aerosol output reductions of up to 30% have been measured. In the worst case, water ingress may also lead to a complete short circuit in which the operation of the vibration head fails. More specifically, water ingress may lead to a reduced parallel electrical resistance value, for example of 1 kΩ, compared to an electrical resistance value of the vibration head, for example of 470 kΩ.

Water ingress into the vibration head thus leads to an additional electrical resistance component, and thus changes the electric energy storage capacity of the vibration head 210. This change in the electric energy storage capacity of the vibration head 210 due to water ingress may be detected by the detection unit due to a corresponding change in the measured discharge profile. In other words, the electric energy storage capacity parameter τ2 is reduced as a function of the amount of water ingress and thus may be detected during repeated measurements in the activation mode. Then, a corresponding warning may be provided by the notification unit 140 to clean or replace the vibration head 210.

According to a further embodiment the determination unit 130 may be further configured to determine a temperature of the vibration head 210. A temperature of the vibration head may reach up to θ=70° C. in extreme operation conditions. Since the electrical parameters of the vibration head, such as the capacitance and/or inductance are temperature dependent, this temperature dependence may influence a voltage discharge profile, and the determination unit 130 is configured to determine a temperature based on the detected electric energy storage capacity parameter. This is an indirect temperature determination which is based on the temperature-dependent capacitance of the vibration head 210. The electric energy storage capacity parameter τ2 thus becomes temperature dependent, i.e. τ2=τ2(θ), and typically the electric energy storage capacity parameter τ2 correlates with the temperature, i.e. an increase in the temperature of the vibration head 210 is associated with an increase (and in some cases a decrease) in the electric energy storage capacity parameter τ2. In another case i.e. an increase in the temperature of the vibration head 210 is associated with phases with a decrease and an increase in the electric energy storage capacity parameter τ2.

As such, by providing the controller 100 with a temperature-electric energy storage capacity parameter τ2 characteristic, for example in a storage unit 150 (to be further discussed below), the determination unit 130 can determine the temperature of the vibration head 210 based on the detected electric energy storage capacity parameter τ2. This functionality is advantageous because it may avoid the provision of an individual temperature sensor at or near the vibration head 210. In addition, at least some medicaments or drugs should not be aerosolized above a certain temperature due to an altered efficacy, integrity or safety of the medicament, drug, or its administration. Therefore, the controller 100 may further be provided with a controlling unit 160 (to be further discussed below) which operates to stop the operation of the aerosol generator 200 when the indirectly detected temperature reaches a medicament/drug specific and/or vibration head specific temperature threshold. Therefore, an overheating of the vibration head 210 may be appropriately avoided. Such an overheating state may also be indicated at the notification unit 140.

According to a further embodiment, the determination unit 130 may use another mechanism to determine a vibration head type. For this mechanism, the electric contacting element 300 is provided with a plurality of electric contacting sub-elements, for example 4 individual electric cables having corresponding 4 cable pins (compare with FIG. 2B) or the like. The plurality of electric contacting sub-elements of the electric contacting element 300 thus provides a plurality of different ways to electrically connect a vibration head 210 with the controller 100. For the example of 4 pins, i.e. pin 1, pin 2, pin 3, and pin 4, a first vibration head type may thus be electrically connected and operated via pin 1 and pin 4, while a second vibration head type may thus be electrically connected and operated via pin 2 and pin 3.

Based on such a configuration of the vibration head types, the detection unit 120 of the controller 100 may perform respective test pulse measurements, as explained above, for the plurality of combinations, e.g. a first test pulse measurement with regard to pin 1 and pin 4, a second test pulse measurement with regard to pin 1 and pin 3, a third test pulse measurement with regard to pin 2 and pin 3, etc. Each of such a specific combination of electric contacting sub-elements is associated with a specific vibration head type.

On the basis of such a unique identification of the vibration head type, the detection unit 120 is further configured to detect an electric energy storage capacity parameter related to the connected electric contacting element for a plurality of the specific combinations of the electric contacting sub-elements, e.g. by applying respective test pulses to the respective combinations of pins.

If a vibration head 210 is connected, then applying a test pulse to one of the specific combinations will result in detecting an electric energy storage capacity parameter that indicates the presence of a vibration head, as explained above, while the other ones of the specific combinations will result in detecting an electric energy storage capacity parameter that indicates that no vibration head is present. Based on the above unique association between combinations of electric contacting sub-elements with a specific vibration head type, the determination unit 130 is thus able to determine the connected vibration head type.

The storage unit 150 of FIG. 8 may also store a plurality of vibration head type dependent configuration parameters. The configuration parameters may refer to head-type dependent electric parameters (voltage, current, and/or frequency) for operating the vibration head. Then, the controlling unit 160 of FIG. 8 may select, based on the determined vibration head type, one of the vibration head type dependent configuration parameters, and control the connected vibration head 210 of the aerosol generator 200 to generate aerosol based on the selected vibration head type dependent configuration parameter. As such, the appropriate electrical drive parameters are used for generating the aerosol and an appropriate aerosol quality may be ensured. In addition, a single controller 100 may operate with a variety of different vibration head types, and it is therefore no longer required to provide respective controllers for each of the different vibration head types.

Based on the above, a cost-efficient way to determine whether a vibration head is connected with the controller of the aerosol generator is provided. The controller may be used, without further programming, with regard to different vibration head types, and thus simplifies the usability.

FIG. 9 shows a controller 100 for an aerosol generator 200 according to another embodiment of the present invention. This embodiment relates to an inline aerosol generator 200 which together with the controller 100 is configured to treat diseases of the respiratory system in a hospital environment. Here, FIG. 9 further shows a connection cord as an example of the electric contacting element 300, a power adaptor 400, and a mounting strap 500. Here, a vibration head is placed in (and may be removed from) the aerosol generator 200, and the inline aerosol generator 200 may be used within a standard ventilator circuit for intubated patients. Here, the nebulizer head of the inline aerosol generator 200 is connected by the connection cord 300 to the controller 100 by plugging one end of the connection cord into the inline aerosol generator 200 and by plugging the other end into the controller 100. A LED light or the like (a notification unit) 140 will illuminate if the inline aerosol generator 200 is connected correctly, i.e. if it is determined by the above detection mechanism that the nebulizer head is connected with connection cord 300 based on a determined electric energy storage capacity parameter. In addition, the notification unit 140 will indicate a specific determined vibration head type, for example using green light for Type 1, a blue light for Type 2, etc.

The mounting strap 500 can be fixedly attached to the controller 100, for example by being integrally formed with it by injection molding. Alternatively, the mounting strap 500 can be fixedly attached to the controller 100 by the mounting strap being clamped by an opening of the controller 100, or it could be latched inside an opening of the controller 100 by means of latches provided on the mounting strap 500 and/or the controller 100. The skilled person can conceive of further ways of fixedly attaching the mounting strap 500 to the controller. Such a fixed attachment is advantageous, for example since it is capable of reliably preventing the controller 100 from falling to the floor when hung from the mounting strap 500.

An alternative, advantageous way of attaching the mounting strap 500 to the controller 100 is to attach the mounting strap 500 to the controller 100 so that it can be detached from the controller 100 without the use of tools. Such an attachment can be achieved by means of latching or clamping the mounting strap 500 in the manner described in the preceding paragraph. Such a detachable attachment is advantageous in that it allows for removing the mounting strap 500 from the controller 100 so that the mounting strap 500 can be cleaned separately from the controller 100. This is particularly important in hospital environments, where hygiene is a paramount concern.

In the embodiment shown in FIG. 9, the mounting strap 500 is detachable, preferably has an elongated shape and is made from a resilient rubber composite. The respective ends of the mounting strap 500 are provided with end portions having a roughly rectangular cross-section (measured perpendicular to the longitudinal direction of the mounting strap 500) which can be inserted into a correspondingly shaped opening of the controller 100. At the ends of the end portions, the cross sectional area of the end portions is increased, so as to keep the end portions positioned inside the opening of the controller 100. It is to be noted that the shape and the specific details of the end portions of the mounting strap 500 can be chosen as appropriate and are not limited to the specific details given above.

Further, the controller 100 of FIG. 9 may offer various options to place it in a secure position. The controller 100 may, for example, be placed on a flat surface. The controller 100 may further be attached in a hanging position by means of the supplied mounting strap 500. The controller 100 may further be provided with a storage element where the connection cord can be stored between treatments.

The invention claimed is:

1. Controller for an aerosol generator having a vibration head for generating an aerosol, the controller comprising:
   a connection unit for connecting an electric contacting element, the electric contacting element being connectable with the vibration head;
   a detection unit for detecting an electric energy storage capacity parameter related to the connected electric contacting element, the electric energy storage capacity parameter being related to at least one of an electric capacity and inductance storable in the vibration head and the electric contacting element; and
   a determination unit for determining whether the vibration head is connected with the electric contacting element based on the determined electric energy storage capacity parameter.

2. The controller according to claim 1, wherein the determination unit is configured to determine that the vibration head is connected with the electric contacting element when the detected electric energy storage capacity parameter exceeds a predetermined threshold.

3. The controller according to claim 1, wherein the determination unit is further configured to determine a vibration head type.

4. The controller according to claim 3, wherein the determination unit is configured to determine the vibration head type by comparing the detected electric energy storage capacity parameter with a plurality of electric energy storage capacity parameter ranges.

5. The controller according to claim 3, wherein the electric contacting element is provided with a plurality of electric contacting sub-elements and the vibration head type is identified by using a specific combination of the plurality of electric contacting sub-elements.

6. The controller according to claim 5, wherein
   the detection unit is further configured to detect an electric energy storage capacity parameter related to the connected electric contacting element for a plurality of the specific combinations of the electric contacting sub-elements; and
   the determination unit is further configured to determine the vibration head type based on the detection of the electric energy storage capacity parameters of the plurality of the specific combinations of the electric contacting sub-elements.

7. The controller according to claim 3, further comprising:
   a storage unit for storing a plurality of vibration head type dependent configuration parameters;
   a controlling unit for selecting, based on the determined vibration head type, one of the stored vibration head type dependent configuration parameters, and for controlling the vibration head of the aerosol generator to generate aerosol based on the selected vibration head type dependent configuration parameter.

8. The controller according to claim 1, wherein the electric energy storage capacity parameter is detected based on a detected discharge profile responsive to a mono-polar or bi-polar electric pulse.

9. The controller according to claim 1, further comprising:
   a notification unit for notifying a user, via at least one of a visual, audio, or a haptic feedback, of a determination result of the determination unit.

10. The controller according to claim 1, wherein the determination unit is further configured to determine water ingress into the vibration head.

11. The controller according to claim 1, wherein the determination unit is further configured to determine a temperature of the vibration head based on the detected electric energy storage capacity parameter.

12. The controller according to claim 1, wherein the electric contacting element comprises at least one of an electronic cable, a connector, a print circuit, a circuit path, a conductive polymer, an electric wire, a pin, and/or a plug.

13. The controller according to claim 1, wherein the detection unit is configured to detect the electric energy storage capacity parameter in a standby operation mode of the vibration head.

14. The controller according to claim 1, wherein the detection unit is configured to detect the electric energy storage capacity parameter in an activation operation mode of the vibration head.

* * * * *